United States Patent [19]
Gay et al.

[11] 4,104,173
[45] Aug. 1, 1978

[54] GELLING AGENTS FOR HYDROCARBON COMPOUNDS

[75] Inventors: Robert L. Gay, Portland, Oreg.; Richard J. Schlott, Arlington Heights; James E. Burroughs, Mt. Prospect, both of, IL

[73] Assignee: Borg-Warner Corporation, Chicago, Ill.

[21] Appl. No.: 606,264

[22] Filed: Aug. 20, 1975

Related U.S. Application Data

[63] Continuation-in-part of Ser. No. 306,773, Nov. 15, 1972, abandoned, which is a continuation-in-part of Ser. No. 209,401, Dec. 17, 1971, abandoned.

[51] Int. Cl.$^2$ ................................................ C09K 3/00
[52] U.S. Cl. ............................... 252/8.55 R; 252/32.5; 252/316; 44/7 D; 166/308; 260/448 R
[58] Field of Search ............. 260/448 R; 252/8.55 R, 252/32.5, 316; 44/7; 166/308, 283

[56] References Cited

U.S. PATENT DOCUMENTS

| | | | |
|---|---|---|---|
| 4,007,128 | 2/1977 | Poklacki | 252/8.55 R X |
| 4,038,207 | 7/1977 | Poklacki | 252/8.55 R X |

*Primary Examiner*—Edward A. Miller
*Assistant Examiner*—J. L. Barr
*Attorney, Agent, or Firm*—Richard J. Schlott

[57] ABSTRACT

In complete, non-stoichiometric aluminum salts of alkyl orthophosphates, when neutralized with a second basic compound, form pseudo double salts which are capable of gelling hydrocarbons when present in low concentrations. The resulting gelled hydrocarbons are useful in cracking or fracturing treatments of oil wells, and exhibit reduced fluid friction in high shear flow systems.

5 Claims, No Drawings

GELLING AGENTS FOR HYDROCARBON COMPOUNDS

REFERENCE TO RELATED APPLICATIONS

This application is a continuation-in-part of Ser. No. 306,773, filed Nov. 15, 1972, now abandoned, which was a continuation-in-part of Ser. No. 209,401, filed Dec. 17, 1971, now abandoned.

BACKGROUND OF THE INVENTION

This invention is directed to the use of particular pseudo double salts of alkyl orthophosphates as gelling agents for hydrocarbons and to a method for gelling liquid hydrocarbons. More particularly, the invention is directed to pseudo double salts of alkyl orthophosphates prepared by first reacting a mixture of alkanols and/or alkenols with phosphorus pentoxide then reacting the alkyl orthophosphate with from 25 to 75% of a stoichiometric equivalent of a basic aluminum compound, followed by neutralization with a second base. These pseudo double salts are efficient gelling agents for hydrocarbons and effect a reduction in fluid friction in high shear flow of hydrocarbons.

Prior to the instant invention, there were a variety of aluminum salts of specific orthophosphates which were used as gelling agents in the preparation of hydrocarbon gels for use in oil well cracking and for other end uses. Examples of dialkyl monohydrogen orthophosphates used as gelling agents in the aluminum form may be found in U.S. Pat. Nos. 3,494,949, 3,505,374 and 3,575,859 issued to Monroe. In U.S. Pat. No. 3,757,864, stoichiometric aluminum salts of orthophosphates are disclosed as fluid friction reducing agents and as gelling agents for hydrocarbons. Related salts of acid hydrocarbyl orthophosphates of titanium, zirconium and hafnium may be found in U.S. Pat. Nos. 3,338,935 issued to Kerschner and 3,334,978 issued to Revurkas. The latter mentioned salts of hydrocarbyl compounds are used as fuel additives rather than as gelling agents.

The aforementioned aluminum salts of dialkyl monohydrogen orthophosphates have exhibited certain disadvantages as gelling agents. One of the major disadvantages has been that these agents are difficult to dissolve and fail to disperse throughout the hydrocarbon and a uniform gel difficulty obtained. The inability to disperse the gelling agent caused the gel to form in a sequestered portion of the liquid hydrocarbon solution with no effect on the remaining hydrocarbon composition. In order to completely disperse the gelling agent, it was normally necessary to heat the hydrocarbon solution to a sufficiently high temperature to disperse the agent throughout and then allow the composition to cool to that point where a gel would form.

The control of the amount of gelation was also somewhat lacking in most prior art systems because there was no efficient way to cause a gel to form at the proper point required for a given end use. Thus, the composition would form a gel only with the total gelling agent present and control over the physical properties of the completed gel was somewhat lacking.

SUMMARY OF THE INVENTION

It has now been found that particular alkyl orthosphosphates may be first converted to an acidic partial aluminum salt by reacting the alkyl orthophosphate with a basic aluminum compound that when further reacted with a second basic compound to neutralize the remaining acidity gives a pseudo double salt of the alkyl orthophosphate which is an effective gelling agent for hydrocarbons. The preparation may be carried out ex-situ to give the pseudo double salt which then is mixed with a hydrocarbon to effect gelation, or more preferably the acidic partial aluminum salt may be first prepared and mixed into the hydrocarbon to give a non-thickened composition which is then neutralized with the second base to produce the pseudo double salt in situ, thus effecting gelation.

The term pseudo double salt is derived by analogy from the common description of such compounds as the alums which contain two cations and a single anion radical as in $K\,Al(SO_4)_2$. These are discrete neutral double salts which form in stoichiometric whole number ratios of the cations. The pseudo double salts of the instant invention may be described as $M_x\,Al_y$ [Alkyl orthophosphate]$_2$; where $y$ may vary from 0.25 to 0.75 and $x$ will be $3(1-y)$; where M is a mono-valent cation such as sodium or ammonium, and $x$ will be $(3/2)(1-y)$; where $x$ is a divalent ion such as calcium. Unlike conventional double salts, these pseudo double salts are prepared having the two cations present in any proportion which together will be sufficient to neutralize the acidic functions of the anion (alkyl orthophosphate) radicals, and simple whole number ratios of the two cations are not necessary. Both this pseudo double salt character and the unusual physical properties in solution reveal these materials to be quite complex in their actual chemical structure, and they are best characterized in terms of the method of their preparations.

The term gelation or gel is used herein to distinguish over merely thickened solutions which have increased viscosities resulting from dissolved solute. The viscosity of thickened solutions varies with the concentration of the solute, while a gel consistency will not disappear on dilution. The gel structures of interest are sensitive to addition of acids or bases, which break down the structure and thereby cause loss of gel behavior and decrease in viscous character. At high dilutions, the gel properties will not be visibly apparent, however the presence of gel may be detected by standard physical chemical methods.

The mixture of alkyl acid orthophosphates that may be used and converted to the partial aluminum salts in accordance with this invention are represented by the formulas

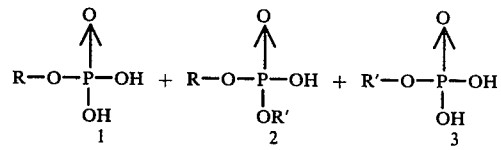

wherein R is a straight chain alkyl group containing one to five carbon atoms and R' is an alkyl or alkenyl group containing six to eighteen carbon atoms.

The desired mixture of alkyl acid orthophosphates is readily prepared by the reaction of a mixture of alcohols of the formulae ROH and R'OH with phosphorus pentoxide ($P_2O_5$) according to methods well known in the art. The product mixture of this reaction will contain approximately equimolar amounts of the dialkyl acid phosphate and monoalkyl acid phosphate, i.e., 1 mole of the phosphate mixture will contain approximately 0.25 m. of structure 1, 0.25 m. of structure 3 (the mono-alkyl acid phosphates) and 0.5 m. of structure 2 (the dialkyl acid phosphate). It will be apparent that the alcohols to be employed in the $P_2O_5$ reaction will be an equimolar mixture of ROH and R'OH, wherein R and R' are defined as above, and both ROH and R'OH may each be single alcohols or mixtures. Other methods for preparing alkyl acid orthophosphates are known which give single compounds or mixtures in other proportions. These may be employed for the purposes of this invention, however, the mixtures employed should contain no less than 10 mole % of each of the above structures.

Compositions within the carbon range indicated are sufficiently soluble to be readily dispersed and are capable of producing gels of high viscosity and uniformity when neutralized. While compositions outside this range of carbon atoms, i.e. either more or less carbons than set forth herein, may be employed, the resulting gels are less satisfactory in that they are normally less effective or of lower viscosity and where R and R' are identical, are virtually ineffective. Thus, when R and R' are octadecyl, the resulting pseudo double salts are waxy solids, difficult to dissolve, form poor and less uniform gels and are ineffective in fluid friction reduction applications. When the gel composition is formed where R and R' are butyl (less carbons), the resulting gel is of very low viscosity and again is ineffective in reducing fluid friction. It thus will be apparent that these pseudo double salts are different in character and behavior from the fully stoichiometric salts disclosed in U.S. Pat. No. 3,757,864.

The acidic partial aluminum salts of the said alkyl acid orthosphosphate mixtures are prepared by reaction with less than a stoichiometric amount of an aluminum compound such as Sodium Aluminate, $Al(OC_3H_7)_3$ or hydrated aluminum oxide. Specifically, the orthophosphate mixtures are converted to the partial aluminum salts by employing up to 75% and preferably less than 50% of a stoichiometric amount of the basic aluminum compound and mildly heating the said mixture to complete the reaction, e.g. from about 100° F. to about 250° F. While the salt-forming reaction may be conveniently carried out in the absence of solvent, inert solvents such as kerosene, diesel fuel, toluene, benzene or naphtha may also be employed, if desired, to moderate the reaction.

The stoichiometric amount of basic aluminum compound is calculated from the free phosphate acid groups present in the alkyl acid orthophosphate mixture employed. In the product mixture from the reaction of a mixture of alcohols with $P_2O_5$ set forth above, there will be 3 acidic hydrogens for every two phosphorus atoms, according to the formula for the generalized reaction between $P_2O_5$ and an alcohol, viz:

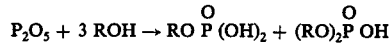
$$P_2O_5 + 3\ ROH \rightarrow RO\overset{O}{\underset{}{P}}(OH)_2 + (RO)_2\overset{O}{\underset{}{P}}OH$$

The stoichiometric amount of a trivalent basic aluminum compound such as $Al(OH)_3$ required to react with the acidic hydrogens would thus be one mole, and the ratio of P/Al in the stoichiometric aluminum salt would be 2/1.

The partial aluminum salts employed for these purposes would be those produced with from 0.75 m. to 0.25 m. of trivalent aluminum compound, which give P/Al ratios of from 2.67/1 to 8/1, preferably from 4/1 (50%) to 8/1. These partial aluminum salts are acidic and do not gel hydrocarbons or produce any noticable thickening when dissolved or dispersed therein. Gelation only occurs when further reacted with a second base to produce the requisite pseudo double salts as set forth hereinbelow.

The level of aluminum employed in these non-stoichiometric or partial aluminum salts affects the character of the resulting gels. When less than about 25% of a stoichiometric amount of aluminum is employed, the subsequent conversion to the pseudo double salt gives gels which are thin and non-coherent. At levels about 50% and particularly above 75%, the resultant compounds are thick, grease-like materials which dissolve in hydrocarbons only with great difficulty, producing some thickening even before gelation.

The partial aluminum salts are then converted to the gelling pseudo double salts by adding sufficient base, such as sodium hydroxide, to neutralize the acidity of the composition. Any inorganic compound that is capable of neutralizing the acid groups in the partial aluminum salt may be used in accordance with this invention. It will be noted that this includes hydroxides, such as alkali metal hydroxides or ammonium hydroxide but is not limited thereto and may, for example, include alkali metal salts of weak acids, as well as oxides and hydroxides of the alkaline earth metals.

Conversion to the gelling pseudo double salt may be carried out by first dispersing the partial aluminum salt in the liquid hydrocarbon and then adding the second basic compound, either as a solid or in water solution, with high speed stirring. Alternatively, the pseudo salt may be prepared ex-situ and then dispersed into the hydrocarbon, however this latter method is not preferred in that the ex-situ prepared salt is also a waxy, difficultly dispersable solid.

The neutralization with the second base to provide the pseudo double salt must be accomplished with precision, and the neutral endpoint is the point at which gelation is complete. For convenience, the endpoint may be detected by use of methyl red indicator, as set forth hereinbelow. The viscosity and degree of gel depends in part on the exactness with which neutralization is completed. Some gel and viscosity increase is noted even before complete neutralization, and the neutralization step may be left incomplete to control the gel and viscosity. To the other extreme, excessive amounts of strong bases will "break" the gel, and reduce the viscosity.

The bases which may be successfully employed include lithium hydroxide, sodium hydroxide, potassium hydroxide, and ammonium hydroxide, either in strong aqueous solutions or where possible, in solid form. Other strong basic materials will be seen to be useful, including the oxides and hydroxides of alkaline earth metals in solid form. Basic salts, those derived from alkali metal hydroxides with weak acids, including sodium carbonate, potassium carbonate, trisodium phosphate, sodium silicate, and borax may also be conveniently employed. Many of these latter salts are additionally advantageous in that while they are sufficiently basic to neutralize the partial aluminum salts to from gels, they are too weakly basic to break resulting gels if employed in excess.

The viscosity of the resulting gel is conveniently controlled by the level of pseudo double salt employed. Some gel character is noted at levels of 0.1 weight percent in the liquid hydrocarbon, while extremely high viscosities are produced at as little as 1.0 weight percent of the combination. Larger amounts, for example up to 10%, may be employed if desired.

The invention as embodied in the method and composition will be more clearly understood in view of the following examples in which all parts are by weight unless otherwise indicated. In many of the following examples, an excess of alcohols is employed in the reaction with $P_2O_5$. It will be understood that this excess is employed to ensure the rapid and complete reaction in the formation of these prior art alkyl acid orthophosphates and the unreacted excess of the alcohols may be removed if desired, however removal is not necessary to practice of this invention. Alternatively, the reaction may be carried out using no excess alcohol if it is desired that the product mixture contain only the alkyl acid orthophosphate.

EXAMPLE I

A dialkyl acid orthophosphate was prepared by reacting one mole of $P_2O_5$ with a mixture of two moles of butyl alcohol and two moles of dodecyl alcohol in the absence of a solvent. The butyl dodecyl acid orthophosphate resulting from this action was used in a preparation of a hydrocarbon gel as follows:

1.0 g. of butyl dodecyl phosphate was added to 125 ml of diesel fuel. The resultant solution was clear. The solution was stirred rapidly and 0.20 ml of a 30% aqueous solution of sodium aluminate was added to the hydrocarbon solution. 5 drops of 30% aqueous solution of sodium hydroxide was thereafter added and the mixture, on stirring, gelled within 30 seconds and was neutral to methyl red. The viscosity of the resultant gel was measured to be 2800 cps as registered on a Brookfield viscometer at 10 rpm, with a No. 2 spindle.

EXAMPLE II

Two hundred grams of butyl dodecyl acid orthophosphate, as prepared in Example I above, were reacted with 6 grams of hydrate $Al_2O_3$ (25% of theory) by heating the mixture at 110° C. for approximately one hour. The water was evaporated off and the resultant partial aluminum salt was cooled. The partial aluminum salt was a viscous oil.

Two grams of the partial aluminum salt as prepared in the paragraph above was added to 250 ml of heptane. The salt dispersed very rapidly in the heptane during stirring at room temperature and no change in viscosity was noted.

Six drops of 20% aqueous ammonium hydroxide was added to the solution with stirring and the resultant gel was neutral to methyl red. The resultant gel was highly viscous and registered a viscosity of 3200 cps on a Brookfield viscometer at 10 rpm with a No. 2 spindle.

EXAMPLE III

Two hundred grams of butyl dodecyl acid orthophosphate was reacted with 13.2 grams of hydrated alumina (54% of stoichiometry) instead of 6 grams as set forth in Example II above. The partial salt was a highly viscous grease. Upon dispersion in fuel oil and neutralization with sodium hydroxide to become neutral to methyl red, there was provided a highly viscous gel which had a viscosity of 2650 cps as measured in Examples I and II above.

EXAMPLE IV

The procedure of Example II was repeated using ethyl octyl acid orthophosphate, ethyl hexadecyl acid orthophosphate methyl oleyl acid phosphate and butyl decyl acid orthophosphate in place of the butyl dodecyl acid orthophosphate. The resulting partial salts were viscous greases and each produced a highly viscous gel, i.e. in the order of 3000 cps when added to fuel oil and neutralized.

EXAMPLE V

Fifty grams of a commercial mixture of n-hexanol, n-octanol and n-decanol, together with 6.12 grams of methanol were dissolved in 22 grams of toluene. To this solution were added 26.9 grams of $P_2O_5$, and the mixture was stirred and heated at 80° C. until all the $P_2O_5$ had dispersed and reacted. To this mixture was added 4.2 grams of hydrated alumina. The stirred mixture was heated to reflux, and the toluene-water azeotrope was distilled until water was no longer produced. On cooling, there resulted a clear, non-viscous toluene solution of partial aluminum salt.

To 125 ml of high-flash naphtha was added 2.0 grams of the solution of the partial salt, formed as set forth above, followed by 2.5 g. of powdered borax. On stirring with high shear in a Waring blendor, a highly viscous gel formed having a viscosity greater than 3600 cps, measured as before.

EXAMPLE VI

A solution of 1.5 grams of butyl octyl acid orthophosphate in 125 ml of dodecane was prepared. To this solution was added 0.15 grams of aluminum isopropoxide, with vigorous stirring, followed by 5 drops of a 35% aqueous sodium hydroxide solution. The viscous gel formed on stirring at high speed, was neutral to methyl red, and had a viscosity of 2600 cps, measured as in Example I.

EXAMPLE VII

To 125 ml of toluene were added 1.5 grams of the toluene solution of partial aluminum salt prepared as set forth in Example V. On neutralization with aqueous potassium hydroxide, a viscous gel was obtained, neutral to methyl red and having 1800 cps viscosity, measured as in Example I.

EXAMPLE VIII

To 100 ml of liquified propane held in a pressure vessel at 110 psig were added 1.2 ml of the toluene solution of partial aluminum salt prepared as set forth in Example V. On neutralization with 30% aqueous sodium hydroxide, a viscous gel was obtained.

EXAMPLE IX

A solution of the partial aluminum salt of ethyl octyl acid orthophosphate, prepared in Example IV, was made from 125 ml of kerosene and 1.6 g. of the partial salt. To this were added 2.5 g. of trisodium phosphate, which on stirring resulted in a highly viscous gelled mass, having a viscosity greater than 3600 cps, measured as in Example I.

EXAMPLE X

Using the procedure of Example IX, calcium oxide, calcium hydroxide and barium oxide were used in place of the trisodium phosphate. In each case, viscous gels were formed of greater than 1400 cps viscosity and the gel was neutral to methyl red.

EXAMPLE XI

Butyl dodecyl acid phosphate was converted to the partial aluminum salt as in Example II. The partial aluminum salt was further converted to the fully neutralized salt in the absence of solvent by treating with 35% aqueous NaOH, and mixing the waxy mass with a spatula until homogeneous. The resulting wax-like solid was neutral to methyl red indicator. The solid was gel-like, in that heating and stirring with diesel fuel served to form a swollen, viscous mass.

The procedure of Example XI serves to illustrate the ex situ method of first preparing the partial aluminum salt, then neutralizing with a second base to form the pseudo double salt in the substantial absence of a liquid hydrocarbon. The ex situ prepared pseudo double salt will, when dispersed in a liquid hydrocarbon, produce a gel, however the dispersion of this ex situ prepared material is difficult at best, and this method of preparation is not preferred.

EXAMPLE XII

Five solutions of the partial aluminum salt of ethyl octyl acid phosphate, prepared as in Example IV, were made in diesel fuel at 0.1 weight percent, 0.5 weight percent, 2 weight percent, 5 weight percent and 10 weight percent. On neutralization with sodium hydroxide to a methyl red indicator end-point, gels formed in all cases. The 0.1 weight percent case had a viscosity near 300 cps, and the 0.5% near 900 cps, while the remaining three had viscosities too great to measure. The 5% and 10% cases were further non-pourable, nearly solid masses.

EXAMPLE XIII

To 250 ml of kerosene in a Waring Blendor were added 2.0 g. of the partial aluminum salt of butyl octyl acid orthophosphate prepared in Example IV. The mixture was stirred at high speed while 6 drops of 35% aqueous caustic (NaOH) were added. The viscosity of the mixture at this point in the neutralization was determined to be 950 cps, measured as before, and had a slight gel character. This mixture was acid to methyl red. The mixture was again stirred, and two more drops of 35% aqueous caustic were added. The mixture at this point had a viscosity of 2100 cps, and substantial gel character, and was acid to methyl red. On addition at one more drop of 35% aqueous caustic, the viscosity of the gel exceeded 3600 cps, and was neutral to methyl red. On addition of 3 more drops of 35% aqueous caustic with high speed stirring, the mixture lost most gel character, had a viscosity of 550 cps and was basic to methyl red and basic to phenophtholein.

It will be apparent from the foregoing specific examples that other variations in structure and neutralizing base may be employed to produce the gelled compositions contemplated by this invention.

Gelled liquid hydrocarbons produced by this invention are highly useful in oil well treatment as fracturing fluids in the treatment of subterranean formations. The characteristics of the gelled hydrocarbons of this invention permit the transport of large volumes of proppants into the fractures of oils wells to provide wide packed fractures in oil bearing formations. This is of particular advantage in producing high permeability formations.

EXAMPLE XIV

Ten thousand gallons of No. 1 diesel fuel were gelled with 120 gallons of the partial aluminum salt of methyl octyl acid orthophosphate described in Example V and 25 gallons of 35% aqueous sodium hydroxide by first dispersing the partial salt in the fuel, then adding in the aqueous sodium hydroxide with high shear mixing. The gelled fuel had a viscosity of 2100 cps, measured as in Example I and was neutral to methyl red indicator.

The gelled composition was pumped, with the addition of proppant (sand) into an oil producing formation 50 feet in width at a depth 9480 feet. The formation was sand stone having a permeability of 50 millidarcies and porosity of 25%. The pumping rate was 15–20 bpm and 8–12 sand was added according to the following schedule:

first 2,000 gals. at 0 pounds per gallon;
second 2,000 gals. at 1 pound per gallon;
third 2,000 gals. at 2 pounds per gallon;
fourth 2,000 gals. at 3 pounds per gallon;
fifth 2,000 gals. at 4 pounds per gallon.

The well, after being closed for one day, was found to produce at 230 BOPD (barrels of oil per day). This was more than a 3 fold increase in production from the 76 BOPD rate prior to this treatment. It will be recognized that both the heat of the well and well fluids will thin the gelled liquid hydrocarbons of this invention while they are in the well. In the instant case the 200 barrels of gelled fuel oil were substantially removed along with crude oil in the first two days after fracturing.

This action is desirable in that well production cannot be blocked by these gels and the gells are capable of being removed with the production of the well. Thus, elaborate flushing post treatment is not required.

As previously mentioned, the gelled hydrocarbons of this invention have increased pumpability by virtue of a reduction in the fluid friction normally associated with the flow of fluids through tubing and pipe. This drag-reducing property is extremely useful in that it permits increases in fluid throughput in a pipe with no increase in power requirement. Alternatively, the reduction of fluid friction in a pipe permits a reduction in energy expended while maintaining a constant flow. The degree of fluid friction reduction produced depends both on concentration of the gelling component and on the fluid velocity in the pipe, as shown in the tabulated data of Example XV set forth in Table I below. Fluid friction reduction, or drag reduction, is calculated by $$\% \, DR = \frac{\Delta P_i - \Delta P_o}{\Delta P_i} \times 100$$

EXAMPLE XV

The partial aluminum salt of butyl octyl acid phosphate was prepared in the same manner and by the same procedure described in Example II for butyl dodecyl acid phosphate. The partial salt was dissolved in 30 gallons of diesel fuel at 12,000 VPPM and carefully neutralized with 30% aqueous sodium hydroxide. The resulting gel was then added to diesel fuel to give the concentrations indicated in the table, after thorough mixing. The fluid was pumped through either of two pipes, one of 0.273 in. internal diameter, and one of 0.906 in., each having pressure measurement taps separated by 20 ft. along the length of the pipe. Pressure drops at several flow rates were measured, and the drag reduction in percent was calculated and is reported in the tabulated data.

Table I

Drag Reduction as a Function of Concentration of Partial Aluminum Salt of Octyl Acid Phosphate Gel Agent and Flow Rate

| Fluid Velocity Ft/Sec | $\Delta P_i$ (psi) Base Fluid | [Gel Agent] VPPM | $\Delta P_o$ (psi) Treated Fluid | Drag Reduction % | Pipe Diameter Inch |
| --- | --- | --- | --- | --- | --- |
| 5  | 1.08 | 300 | 0.56 | 46 | 0.907 |
| 10 | 3.47 | 300 | 1.59 | 54 | 0.907 |
| 15 | 28   | 300 | 10.6 | 62 | 0.273 |
| 30 | 98   | 300 | 54   | 55 | 0.273 |
| 5  | 1.08 | 900 | 0.54 | 50 | 0.907 |
| 10 | 3.47 | 900 | 1.12 | 68 | 0.907 |
| 15 | 28   | 900 | 6.4  | 77 | 0.273 |
| 30 | 98   | 900 | 22   | 79 | 0.273 |

EXAMPLE XVI

A gel was formed in 10 gallons of diesel fuel by dissolving 12,000 VPPM of the partial aluminum soap of butyl octyl acid phosphate described in Example XV in the diesel fuel and carefully neutralizing with 30% aqueous caustic. The fully-formed gel was then added to nine volumes of crude oil to give a final concentration of 1,200 VPPM of the gel agent. In flow measurements in the pipe flow apparatus, using the 0.907 in. diameter pipe, a drag reduction value of 37% was observed.

EXAMPLE XVII

Butyl cetyl acid phosphate and Di octyl acid phosphate were prepared as in Example I and converted to the corresponding partial aluminum salts by the technique employed in Example II. Each were dissolved in 25 gallons of diesel fuel at a concentration of 1,000 VPPM, and carefully neutralized. Drag reduction data were obtained for each as before. The gel from the butyl cetyl acid phosphate produced a drag reduction value of 41%, measured in a 1/8 in. diameter pipe line, while the di octyl acid phosphate gel gave no measureable drag reduction.

It will be noted that useful reductions in fluid friction were observed even at very low, nearly trace concentrations of gelling agents and at very low velocities. At concentrations of as little as 300 VPPM (0.025 weight percent) no gel character or appearance was noted, yet drag reductions as great as 62% were measured. This behavior is unique in that until this time, fluid friction reduction phenomenon in hydrocarbon fluids had been observed only for polymeric additives such as polyisobutylene and high molecular weight EPR.

The invention will thus be seen to be the preparation of pseudo double salts of alkyl acid orthophosphates prepared by first reacting a mixed alkyl acid orthophosphate with from 25% to 75% preferably from 25% to 50% of a stoichiometric amount of a basic aluminum compound to give a partial aluminum salt, followed by neutralization with a second base to give a pseudo double salt which will gel hydrocarbons, and a method for preparing gelled hydrocarbons containing the pseudo double salt in a concentration range of from 0.025 wt. % to 10 wt. %. At the lowest concentrations, the presence of gel is evidenced by certain physical properties of the composition including flow properties, while at greater concentrations, particularly above 0.1 wt. %, the hydrocarbon is visibly gelled.

The gels are useful where high flow properties and/or thickened characteristics are needed, as for example in the hydraulic fracturing of oil wells.

Though the invention has been described with respect to specific examples this is by way of illustration and not limitation and the scope of the invention is delineated by the claims which are attached hereto and made a part hereof.

We claim:

1. A method of making a gelled hydrocarbon composition comprising the steps of
   (a) preparing a mixture of alkyl acid orthophosphates by reacting phosphorus pentoxide with a mixture of at least two alcohols wherein at least one alcohol is selected from the group consisting of $C_1$ to $C_5$ n-alkanols and at least one alcohol is selected from the group consisting of $C_6$ to $C_{18}$ alkanols and $C_6$ to $C_{18}$ alkenols,
   (b) reacting said mixture of alkyl acid orthophosphates with a basic aluminum compound selected from the group consisting of hydrated alumina and aluminum alkoxides in a ratio of from 2.67 to 8 gram atoms of phosphorus per gram atom of aluminum to produce a partial aluminum salt of the alkyl acid orthophosphates,
   (c) adding from 0.1 to about 10 parts by weight of said partial aluminum salt to 100 parts by weight of a liquid hydrocarbon, and
   (d) adding thereto sufficient amount of a second base selected from the group consisting of alkali metal hydroxides, alkali metal oxides, ammonium hydroxide, alkaline earth metal hydroxides, alkaline earth metal oxides, and alkali metal salts of weak acids to neutralize the remaining acidity.

2. The method of claim 1 further comprising diluting said gelled hydrocarbon composition with from 1 to about 1,000 volumes of a liquid hydrocarbon.

3. A liquid hydrocarbon composition comprising a liquid hydrocarbon and a minor amount of a gelling agent consisting of the pseudo double salts of alkyl acid orthophosphates with aluminum and a second ion selected from the group consisting of alkali metal, alkaline earth metal and ammonium ions, said pseudo double salt prepared by the steps of
   (a) preparing a mixture of alkyl acid orthophosphates by reacting phosphorus pentoxide with a mixture of at least two alcohols wherein at least one alcohol is selected from the group consisting of $C_1$ to $C_5$ n-alkanols and at least one alcohol is selected from the group consisting of $C_6$ to $C_{18}$ alkanols and $C_6$ to $C_{18}$ alkenols,
   (b) reacting said mixture of alkyl acid orthophosphates with a basic aluminum compound selected from the group consisting of hydrated of alumina and aluminum alkoxides in a ratio of from 2.67 to 8 gram atoms of phosphorus per gram atom of aluminum to produce a partial aluminum salt of the alkyl acid orthophosphates, (c) adding from 0.1 to about 10 parts by weight of said partial aluminum salt to 100 parts by weight of a liquid hydrocarbon, and (d) adding thereto sufficient amount of a second base selected from the group consisting of alkali metal hydroxides, alkali metal oxides, ammonium hydroxide, alkaline earth metal hydroxides, alkaline earth metal oxides, and alkali metal salts of weak acids to neutralize the remaining acidity.

4. A pseudo double salt of an alkyl acid orthophosphate prepared by the steps of (a) preparing a mixture of alkyl acid orthophosphates by reacting phosphorus pentoxide with a mixture of at least two alcohols wherein at least one alcohol is selected from the group consisting of $C_1$ to $C_5$ n-alkanols and at least one alcohol is selected from the group consisting of $C_6$ to $C_{18}$ alkanols and $C_6$ to $C_{18}$ alkenols, (b) reacting said mixture of alkyl acid orthophosphates with a basic aluminum compound selected from the group consisting of hydrated alumina and aluminum alkoxides in a ratio of from 2.67 gram atoms of phosphorus per gram atom of aluminum to produce a partial aluminum salt of the alkyl acid orthophosphates, and (c) adding thereto sufficient amount of a second base selected from the group consisting of alkali metal hydroxides, alkali metal oxides, ammonium hydroxide, alkaline earth metal hydroxides, alkaline earth oxides, and alkali metal salts of weak acids to neutralize the remaining acidity.

5. The pseudo double salt of claim 4 wherein the neutralization Step C is carried out in the presence of from 9 parts by weight to 4,000 parts by weight of a liquid hydrocarbon per 1 part by weight of partial aluminum salt.

* * * * *

UNITED STATES PATENT OFFICE
CERTIFICATE OF CORRECTION

PATENT NO. : 4,104,173

DATED : August 1, 1978

INVENTOR(S) : ROBERT L. GAY and RICHARD J. SCHLOTT and JAMES E. BURROUGHS

It is certified that error appears in the above-identified patent and that said Letters Patent are hereby corrected as shown below:

The following references were cited:

| | | | |
|---|---|---|---|
| 3,494,949 | 2/70 | Monroe, et al | 260/448R |
| 3,757,864 | 9/73 | Crawford, et al | 252/8.55R |
| 3,692,676 | 9/73 | Cutler, et al | 166/308 |
| 3,900,070 | 8/75 | Chatterji, et al | 252/8.55R |
| 3,575,859 | 4/71 | Monroe | 152/50 |

Signed and Sealed this

Sixth Day of March 1979

[SEAL]

Attest:

RUTH C. MASON
Attesting Officer

DONALD W. BANNER
Commissioner of Patents and Trademarks